United States Patent [19]
Kohn et al.

[11] Patent Number: 5,744,492
[45] Date of Patent: Apr. 28, 1998

[54] METHOD FOR INHIBITING ANGIOGENESIS

[75] Inventors: Elise C. Kohn, Olney; Lance A. Liotta, Potomac; Riccardo Alessandro, Bethesda, all of Md.

[73] Assignee: United States of America, Washington, D.C.

[21] Appl. No.: 209,651

[22] Filed: Mar. 10, 1994

Related U.S. Application Data

[63] Continuation-in-part of Ser. No. 123,614, Sep. 17, 1993, abandoned.

[51] Int. Cl.$^6$ .................................................. A61K 31/41
[52] U.S. Cl. ...................... 514/359; 514/356; 514/648; 514/650
[58] Field of Search .................................. 514/359, 356, 514/648, 650

[56] References Cited

U.S. PATENT DOCUMENTS

| | | |
|---|---|---|
| 4,590,201 | 5/1986 | Bochis et al. |
| 4,816,469 | 3/1989 | Bochis et al. |
| 4,847,257 | 7/1989 | Hupe et al. |
| 5,132,315 | 7/1992 | Kohn et al. |
| 5,498,620 | 3/1996 | Kohn et al. ........................ 514/359 |

OTHER PUBLICATIONS

Aznavoorian, et al., *J. Cell Biol.*, 110:1427–1438 (1990).
Savarese, et al., *J. Biol. Chem.*, 30:21928–21935 (1992).
Kohn, et al., *J. Natl. Cancer Inst.*, 82:54–60 (1990).
Kohn, et al., *Biochem. Biophys. Res. Comm.*, 166:757–764 (1990).
Kohn, et al., *Cancer Res.*, 52:3208–3212 (1992).
Gospodarowicz, *Annal New York Acad. Sci.*, 638:1–9 (1992).
Jaye, et al., *Biochim. Biophys. Acta.*, 1135:185–199 (1992).
Minniti, et al., *J. Biol. Chem.*, 267:9000–9004 (1992).
Brown, et al., *Cancer Research*, 50:6184–6191 (1990).
Rifkin, et al., *J. Cell Biol.*, 109:1–6 (1989).
Kubota, et al., *J. Cell Biol.*, 107:1589–1598 (1988).
Albini, et al., *Int. J. Oncol.*, 1:723–730 (1992).
Taylor, et al, *Nature*, 297:307–311 (1982).
Kohn, E., et al., "Aging Issues in Invasion and Metastasis," *Cancer*, 71(5):552–557 (15 Jan. 1993).

*Primary Examiner*—Keith MacMillan
*Attorney, Agent, or Firm*—Townsend and Townsend and Crew

[57] ABSTRACT

Angiogenesis is a composite of regulated proliferation and regulated invasion occuring in a variety of normal and pathologic conditions. Compound 1 and related analogs are useful for inhibiting angiogenesis in a host and offer a novel approach to the treatment of cancer, diabetic retinopathy, hemangiomata, vasculidities and other diseases associated with angiogenesis.

7 Claims, 6 Drawing Sheets

METHOD FOR INHIBITING ANGIOGENESIS

The present application is a Continuation-In-Part of application Ser. No. 08/123,614, filed Sep. 17, 1993, now abandoned, the contents of which are incorporated herein by reference.

BACKGROUND OF THE INVENTION

Angiogenesis, the formation of new blood vessels, is a composite of regulated proliferation and regulated invasion. It occurs in a variety of normal and pathologic conditions. During angiogenesis, endothelial cells react to stimulation with finely tuned signaling responses. In normal physiological states such as embryonic growth and wound healing, neovascularization is controlled by a balance of stimulatory and inhibitory angiogenic factors. These controls may fail and result in formation of an extensive capillary network during the development of many diseases including cancer, diabetic retinopathy, hemangiomata and vasculidities.

Angiogenic stimuli elicit a response which is composed of protease secretion to facilitate basement membrane remodeling, proliferation of endothelial cells, and endothelial cell migration to form capillary sprouts and for lumen closure. This triad of proteolysis, adhesion and migration make up the process of invasion which is the hallmark of malignancy. Thus, angiogenesis is a form of regulated invasion.

The role of calcium in the regulation of invasion is now emerging. It is a key component of cellular adhesion pathways, important in proteolytic degradation of the basement membrane, and is involved in migration in response to motility factors and extracellular matrix components. See, Aznavoorian, et al., *J. Cell Biol.* 110:1427–1438 (1990); Savarese, et al., *J. Biol. Chem.* 30:21928–21935 (1992); Kohn, et al., *J. Natl. Cancer Inst.* 82:54–60 (1990); and Kohn, et al., *Biochem. Biophys. Res. Comm.* 166:757–764 (1990).

Compound 1, shown below, was originally designed as a coccidiostat (U.S. Pat. No. 4,590,201) and later developed as a cancer treatment agent of particular use in the treatment of peritoneal carcinomatosis of ovarian cancer (U.S. Pat. No. 5,132,315, and Kohn, et al., *J. Natl. Cancer Inst.*, 82:54–60 (1990)). Compound 1 has recently been used to confirm the role of calcium-mediated events in invasion. See, Kohn, et al., *Cancer Res.*, 52:3208–3212 (1992). The components of tumor invasion and normal blood vessel formation (adhesion, proteolysis, migration and proliferation) can be assayed in vitro in the same fashion. However, the difference between invasion of tumor cells into host tissues and the invasive behavior of endothelial cells in neoangiogenesis lies in the regulation of the two processes.

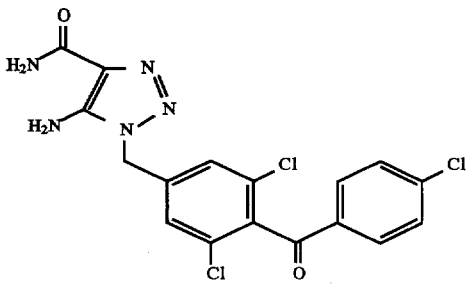

1

Acidic and basic fibroblast growth factors are the best characterized and most potent angiogenic factors described. See, Gospodarowicz, *Annal New York Acad. Sci.* 638:1–9 (1992). Basic FGF exerts its activity through activation of the bFGF receptor kinase with subsequent autophosphorylation of its receptor as well as phosphorylation of other signaling proteins. See, Jaye, et al., *Biochim. Biophys. Acta* 1135:185–199 (1992).

We have now discovered that compound 1 can inhibit bFGF signals and thereby inhibit endothelial cell proliferation and proteolysis in vitro and in vivo. Additionally, compound 1 inhibits endothelial cell adhesion and migration in response to basement membrane components to which it is exposed in vivo during neoangiogenesis.

SUMMARY OF THE INVENTION

It has now been discovered that certain compounds inhibit angiogenesis in vitro and in vivo. These compounds inhibit angiogenesis by inhibiting proliferation of cells in response to serum or basic fibroblast growth factor, by inhibiting adhesion and motility to the basement membrane proteins laminin, fibronectin and type IV collagen, and by inhibiting native and bFGF-induced gelatinase activity.

The present invention provides a method for inhibiting angiogenesis in a host using compound 1 and related analogs. Pharmaceutical application directed to inhibiting angiogenesis offers a novel approach to the treatment of cancer, diabetic retinopathy, hemangiomata, vasculidities and other diseases associated with angiogenesis.

BRIEF DESCRIPTION OF THE DRAWINGS

FIG. 1 shows the effect of compound 1 on basal and bFGF-stimulated HUVEC growth.

FIG. 2 shows the effect on adhesion and migration in response to basement membrane components (fibronectin, laminin, type IV collagen, and thrombospondin).

DESCRIPTION OF THE PREFERRED EMBODIMENT

Figure 1A:
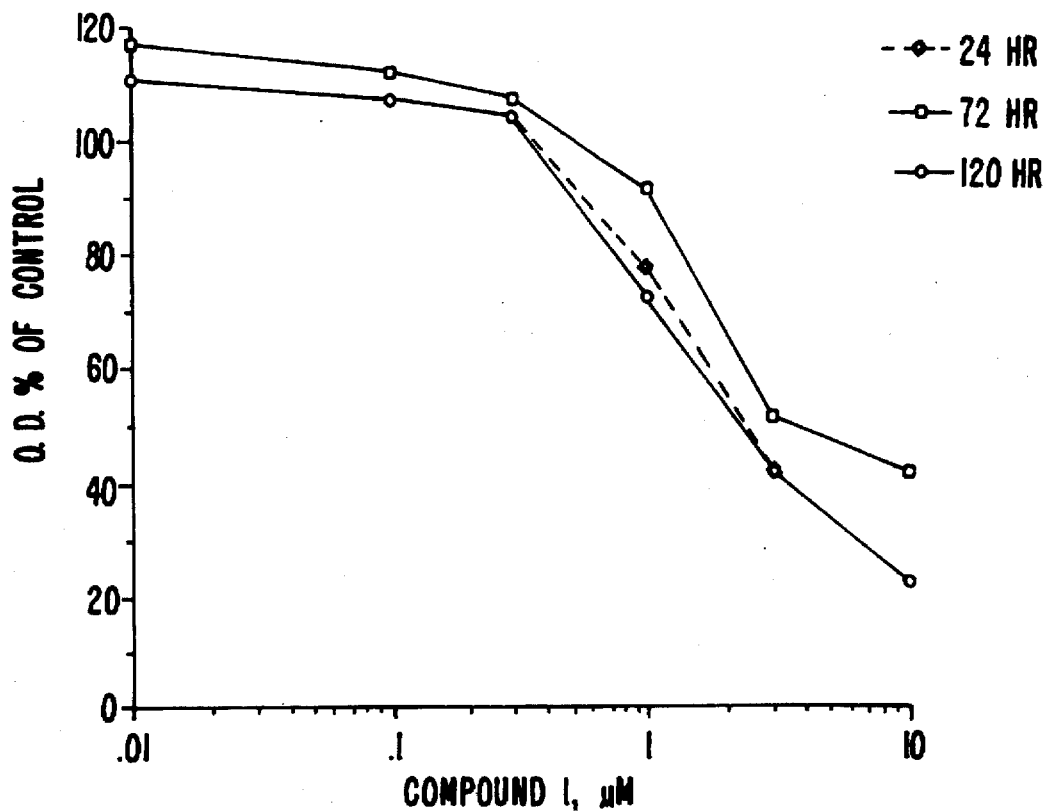
FIG. 1A depicts results using serum with ECGS and FIG. 1B shows results using bFGF in low serum.

The following abbreviations are used herein: MMP, matrix metalloproteinase; bFGF, basic fibroblast growth factor; ECGS, endothelial cell growth supplement; TGF-$\beta_1$, transforming growth factor-$\beta_1$; PLC-$\gamma$, phospholipase C-$\gamma$; SSC, saturated sodium citrate solution; CAM, chick chorioallantoic membrane; HUVECs, human umbilical vein endothelial cells; DMSO, dimethyl sulfoxide; DPBS, Dulbecco's phosphate-buffered saline; FCS, fetal calf serum; EDTA, ethylenediamine tetraacetic acid; BSA, bovine serum albumin; BM, basement membrane; and TIMP-2, tissue inhibitor of metalloproteinase-2.

As used herein, the term "alkyl" refers to a saturated hydrocarbon radical which may be straight-chain or branched-chain (for example, ethyl, isopropyl, t-amyl, or 2,5-dimethylhexyl). Preferred alkyl groups are those containing 1 to 6 carbon atoms. All numerical ranges in this specification and claims are intended to be inclusive of their upper and lower limits.

The term "alkoxy" refers to an alkyl radical as described above which also bears an oxygen substituent which is capable of covalent attachment to another hydrocarbon radical (such as, for example, methoxy, ethoxy, phenoxy and t-butoxy).

The term "aromatic group" refers to a group of unsaturated cyclic hydrocarbons containing one or more rings. The rings are typified by benzene which has a 6-carbon ring containing three double bonds. Groups containing multiple rings may have the rings fused together or linked covalently. Examples of such multiple ring aromatic groups are naphthyl, biphenyl and anthracenyl. The term "aromatic group" also refers to those groups described above which contain heteroatoms, for example, pyridyl and quinoxalyl. Other aromatic groups include certain 5-membered cyclic moieties such as the furan group and the thienyl group. Any of the aromatic groups described herein may be optionally substituted with halogen atoms, or other groups such as nitro, carboxyl, alkoxy and the like.

The term "alkoxyalkyl" refers to an alkoxy radical attached directly to an alkyl group. When used as a linking group, alkoxyalkyl refers to such radicals as —CH$_2$OCH$_2$—, —CH$_2$OCH$_2$CH$_2$—, —CH$_2$CH$_2$CH$_2$OCH$_2$— and —CH$_2$CH$_2$OCH$_2$CH$_2$—. The term "substituted" refers to groups having additional moieties attached, such moieties including halogen atoms, and groups such as nitro, carboxyl, alkoxy, amino, carbamoyl and the like.

The term "effective amount" refers to an amount sufficient to elicit the desired biological response.

The term "host" refers to any organism wherein angiogenesis takes place. Preferred hosts would include any vertebrate species. Particularly preferred hosts are mammals, with humans being the most preferred host.

The present invention provides a method of inhibiting angiogenesis in a host using compounds of formula I.

Y—(CH$_2$)$_p$—Ar$^1$.X—Ar$^2$ (I)

The groups Ar$^1$ and Ar$^2$ are aromatic groups and may be the same or different. Examples of aromatic groups are phenyl, substituted phenyl, naphthyl, and substituted naphthyl.

The symbol X represents a linking group and may be O, S, SO$_2$, CO, CHCN, straight chain alkyl, alkoxy, and alkoxyalkyl.

The symbol Y represents a variety of structures. Some of these structures are represented by formula II:

in which A is N or CH; R$^1$ is hydrogen, —CONH$_2$ (carbamoyl), —CONHR$^5$, —CO$_2$H (carboxyl), —CO$_2$R$^5$, or —SO$_2$NH$_2$; R$^2$ is hydrogen, —NH$_2$ (amino), —NHCOC6H$_5$ (benzamido), —NHCOR$^5$, —NHCHO (formamido), —NHR$^5$, or —N(R$^5$)$_2$ and R$^5$ is lower alkyl of from 1 to 6 carbon atoms. A preferred group for A is N.

Preferred groups for R$^1$ are hydrogen, —CONH$_2$, —CONHR$^5$, and —CO$_2$H. Particularly preferred are —CONH$_2$ and —CO$_2$H. Preferred groups for R$^2$ are —NH$_2$, —NHCOC$_6$H$_5$, —NHCOR$^5$, and —NHR$^5$. Particularly preferred groups for R$^2$ are —NH$_2$ and —NHCOR$^5$.

Other structures for Y are 1,2,4-triazolyl, pyrazinyl, purinyl, pyrimidinyl, 1,2,3-triazolo-{4,5-d}-pyrimidinyl, and their substituted analogs.

The symbol p represents an integer of from 0 to 4.

In certain preferred embodiments, this method uses a compound of formula I in which Y is a radical of formula II, A is N and R$^1$ is —CONH$_2$.

In further preferred embodiments, this method uses a compound of formula I in which Y is a radical of formula II, A is N, R$^1$ is —CONH$_2$, and R$^2$ is —NH$_2$.

In still further preferred embodiments, this method uses a compound of formula I in which p is an integer of from 0 to 2, Ar$^1$ and Ar$^2$ are both substituted phenyl, X is O, CO or CHCN, Y is a radical of formula II, A is N, R$^1$ is —CONH$_2$, and R$^2$ is —NH$_2$.

In the most preferred embodiment, this method uses a compound of formula I in which p is 1, Ar$^1$ is 2,6-dichlorophenyl, Ar$^2$ is 4-chlorophenyl, X is CO, Y is a radical of formula II, A is N, R$^1$ is —CONH$_2$, and R$^2$ is —NH$_2$.

The compounds used in the present inventive method may be prepared using conventional synthetic techniques. Compound 1 can be prepared by the method described in U.S. Pat. No. 4,590,201. Briefly, 2,6-dichloro-4-methylbenzoic acid is converted to its corresponding benzoyl chloride using thionyl chloride in dimethylformamide. Reaction of this benzoyl chloride with chlorobenzene in the presence of aluminum trichloride provides 4-(4-chlorobenzoyl)-3,5-dichlorotoluene. Bromination of the methyl group is carried out using N-bromosuccinimide in the presence of catalytic amounts of dibenzoyl peroxide to provide 4-(4-chlorobenzoyl)-3,5-dichlorobenzyl bromide. The benzyl bromide is then converted to the corresponding benzyl azide using potassium azide. Treatment of the 4-(4-chlorobenzoyl)-3,5dichlorobenzyl azide thus formed with 2-cyanoacetamide in the presence of sodium methoxide provides after workup, 5-amino-1-(4-(4-chlorobenzoyl)-3,5-dichlorobenzyl)1,2,3-triazole-4-carboxamide (Compound 1).

Related analogs can be prepared either by derivatization of compound 1 or by the general approach used for compound 1. Materials and conditions will vary depending on the desired analog. Particular conditions are known to those of skill in the art.

The compounds used in the present inventive method may be administered in any suitable manner, preferably with pharmaceutically acceptable carriers. One skilled in the art will appreciate that suitable methods of administering such compounds in the context of the present invention to an animal are available, and, although more than one route can be used to administer a particular compound, a particular route can often provide a more immediate and more effective reaction than another route. Pharmaceutically acceptable carriers are also well-known to those who are skilled in the art. The optimal choice of carrier will be determined in part by the particular compound, as well as by the particular method used to administer the composition. Accordingly, there is a wide variety of suitable formulations of the pharmaceutical composition of the present invention.

Formulations suitable for oral administration can consist of (a) liquid solutions, such as an effective amount of the compound dissolved in diluents, such as water, saline or PEG 400; (b) capsules, sachets or tablets, each containing a predetermined amount of the active ingredient, as solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, mositening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such as carriers as are known in the art.

The active ingredient, alone or in combination with other suitable components, can be made into aerosol formulations to be administered via inhalation. These aerosol formulations can be placed into pressurized acceptable propellants, such as dichlorodifluoromethane, propane, nitrogen, and the like.

Suitable formulations for rectal administration include, for example, suppositories, which consist of the active ingredient with a suppository base. Suitable suppository bases include natural or synthetic triglycerides or paraffin hydrocarbons. In addition, it is also possible to use gelatin rectal capsules which consist of a combination of the active ingredient with a base, such as, for example, liquid triglyercides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to an animal, particularly a human, in the context of the present invention should be sufficient to effect a therapeutic response in the animal over a reasonable time frame. The dose will be determined by the strength of the particular compound employed and the condition of the animal, as well as the body weight or surface area of the animal to be treated. The size of the dose also will be determined by the existence, nature, and extent of any adverse side-effects that might accompany the administration of a particular compound in a particular animal. In determining the effective amount of the active ingredient to be administered in the treatment or prophylaxis of cancer, the physician needs to evaluate circulating plasma levels, toxicities, and tumor growth inhibition, and evidence of cancer progression.

In the practice of this invention, the compounds can be administered, for example, by intravenous infusion, orally, topically, intraperitoneally, intravesically or intrathecally for treatment of lymphomas, leukemias, and all solid tumors. The compounds could be applied in a suitable vehicle for the local and topical treatment of cancer. Tumors such as basal cell carcinoma and Kaposi's sarcoma could be treated by topical administration of the agents taught herein. Prevention of tumor recurrence by administration of the composition in a manner intended to reach the particular site where such cells are proliferating would be most advantageous. For example, intraperitoneal administration would be a means of treating tumors known to cause peritoneal carcinomatosis. Intravesical treatment of transitional cell carcinoma and topical treatment of mycosis fungoides are further examples of site-directed treatment. Systemic administration may be accomplished by continuous infusion, bolus parenteral treatment, or release from an implanted slow release depot. It is obvious that this method can supplement treatment of cancer by any conventional therapy including cytotoxic agents and biologic response modifiers. The method disclosed may be used in any malignancy as a means of treatment to prevent the transition from in situ to invasive carcinoma or invasive to metastatic carcinoma.

For oral administration, compounds of the present inventive method can be administered at the rate up to 3000 mg/m$^2$ body surface area, which approximates 6 grams/day in the average patient. This can be accomplished via single or divided doses. For intravenous administration, such compounds can be administered at the rate of up to about 2500 mg/m$^2$/d. For intravesical administration, such compounds can be administered at the rate of up to about 2500 mg/m$^2$/d. For topical administration, the rate can be up to about 2500 mg/m$^2$/d. The dose for inhalation/aerosol administration can be up to about 2500 mg/m$^2$/d. Direct intraperitoneal administration can be performed using up to about 3000 mg/m$^2$/d. The dose for reservoir administration to the brain or spinal fluid can be up to about 2000 mg/m$^2$/d. For slow release intraperitoneal or subcutaneous administration, the dose can be up to about 10 g/day in a bolus. For intrathecal administration, the dose can be up to about 2000 mg/m$^2$/d.

The methods taught herein are not restricted to use in treatment of malignancies. Disease conditions such as endometriosis, psoriasis, and eczema which result from localized spread of diseased cells may also be advantageously treated. Additionally, disease states which rely on angiogenesis may also be treated. Diseases of angiogenesis may include the collagen vasculitides (i.e., systemic lupus erthythematosis and rheumatoid arthritis), proliferative nephropathies, neurologic diseases (i.e., dementia and nerve conduction diseases), diseases of transport (i.e., cystic fibrosis), toxic effects of agents (i.e., cisplatin-related neuropathy), cellular dysfunction (i.e., myelodysfunction syndromes), hemangiomata and diabetic retinopathy.

EXAMPLES

Materials

Compound 1 was supplied as a powder by the Developmental Therapeutics Program of the National Cancer Institute (NCI, Bethesda, Md., USA). A 20 mM stock solution was made in DMSO and aliquots were stored at −70° C. For use, a 10 µM solution was prepared daily in media (DMEM), and serial dilutions were made as needed.

Other reagents were either reagent grade or HPLC grade from commercial sources (Sigma Chemical Co., St. Louis, Mo., USA and Aldrich, Milwaukee, Wisc., USA).

Precast 10% SDS-PAGE gels containing 1 mg/mL of gelatin, and 4–20% gradient PAGE gels were purchased from Novex (San Diego, Calif., USA). Recombinant basic fibroblast growth factor (bFGF) and transforming growth factor-β1 (TGF-β$_1$) were from R&D systems (Minneapolis, Minn., USA). Endothelial cell growth supplement (ECGS) and endothelial cell growth factor (ECGF/acidic FGF), fibronectin, laminin, type IV collagen, thrombospondin, and Matrigel were obtained from Collaborative Research (New Bedford, Mass., USA). Anti-phosphotyrosine monoclonal antibody (4G10) was from UBI (Lake Placid, N.Y., USA). $^{32}$P-dCTP for probe labeling was obtained from NEN (Boston, Mass., USA), and $^{125}$I-Protein A was purchased from Amersham (Arlinghton Heights, Ill., USA). Protein-A Sepharose was obtained from Gibco/BRL (Gaithersburg, Md., USA). Fertilized chicken eggs were from Truscow Farms (Chesterton, Md., USA). Equipment and membranes for motility assays were from Neuroprobe (Cabin John, Md., USA).

Cell culture.

Human umbilical vein endothelial cells (H 930) were generously supplied by Dr. Tom Maciag, American Red Cross (Gaithersburg, Md., USA) and were used between passages 9 and 14 to avoid senescence. HUVECs were grown on fibronectin-coated tissue culture plastic (200 μg/150 mm dish) in complete medium (Medium 199 (M-199) containing 5 U/mL preservative-free heparin, 25.5 μg/mL ECGS, 10% fetal bovine serum and 100 U/mL penicillin, 100 μg/mL streptomycin, and 0.25 μg/mL fungizone).

EXAMPLE 1

Dose dependent inhibition of HUVEC proliferation.

This example illustrates the effect of compound 1 on endothelial cell proliferation.

The effect of compound 1 on HUVEC proliferation was examined over a 5 day period of culture. Cell monolayers were incubated with increasing concentrations of compound 1 and evaluated incrementally for growth inhibition.

Growth inhibition of HUVECs by compound 1 was measured by crystal violet nuclear stain. Briefly, 50,000 cells were seeded per well in 24 well plates using complete medium in the presence of increasing concentrations of compound 1 (0.01–10 μM) or DMSO vehicle control (0.1%) and cultures were incubated for 24–120 hours. After incubation, cells were washed carefully with Dulbecco's phosphate-buffered saline (DPBS), fixed and stained with 0.5% crystal violet in 20% methanol. Excess stain was removed with water, the cell monolayers were air-dried, and then bound stain was eluted with a 1:1 solution of 0.1N sodium citrate (pH 4.2): 100% ethanol. Optical density of the eluted samples was determined at 540 nm and the results were expressed as percent of DMSO control cell growth. Data are expressed as percentage of control value and are presented as mean±SEM (n=3).

FIG. 1A shows the results using 10% serum with ECGS. Samples were tested at 24, 72 and 120 hrs after plating the cells. Compound 1 caused a dose-dependent but not time-dependent inhibition of endothelial cell proliferation. The IC$_{50}$ (the concentration at which 50% inhibition is obtained) at 1, 3, and 5 days of culture were 1.31±0.03 μM, 2.14±0.03 μM, and 2.08±0.01 μM, respectively. DMSO vehicle did not influence endothelial cell proliferation.

To evaluate the effect of bFGF on HUVECs growth, cells were plated in low serum medium (1% FCS) in the presence of 10 ng/ml of bFGF and increasing concentrations of compound 1. At the indicated time, cells were fixed, stained, and quantitated as described above.

Figure 1B:
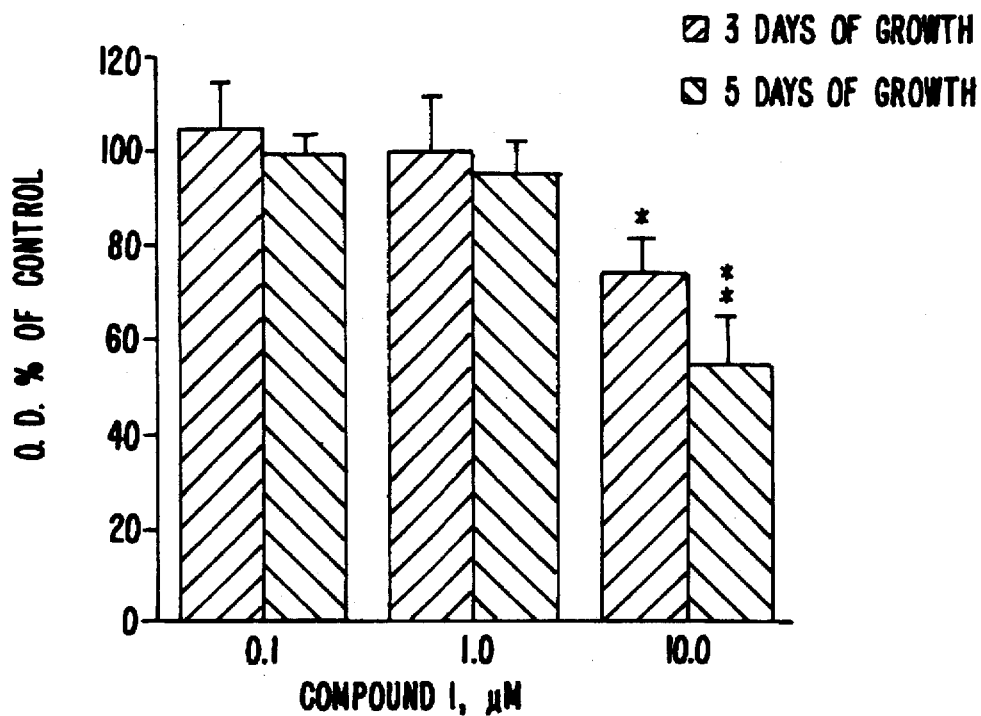

FIG. 1B shows the results using bFGF in low serum (1%). The addition of 10 μM compound 1 caused a statistically significant inhibition of growth of 25% (* P2<0.01) and 45% (** P2<0.005) of control after 3 and 5 days from seeding, respectively.

These results indicate that compound 1 can markedly inhibit proliferation of HUVECs in the presence of standard serum and factor-containing growth conditions and when the HUVECs were primarily dependent upon bFGF for growth stimulation.

EXAMPLE 2

Inhibition of adhesion and stimulated motility.

This example illustrates the effect of compound 1 on HUVEC adhesion and motility to constituent molecules of the basement membrane including laminin, fibronectin and type IV collagen.

Proteolytic remodeling of the endothelial cell basement membrane serves several functions. First, it creates a focus from which capillary buds may sprout in order to reach the angiogenic stimulus. Second, it provides access to basement membrane (BM) constituent glycoproteins such as laminin, fibronectin, type IV collagen and glycoprotein fragments which may be chemotactic stimuli to support endothelial cell migration during vascular sprout formation.

Adhesion of control and compound 1-treated HUVECs to specific substrata was tested as follows. Glass slides coated with specific adhesion substrata were prepared by placement of 10 μL aliquots of 25 nM each fibronectin, laminin, gelatin or type IV collagen into triplicate wells of multichamber slides. Slides were incubated at 37° C. for 2 hours and then air-dried overnight. The following day the slides were blocked with 300 μL of blocking buffer (Tris 50 μM pH 7.8, NaCl 111 mM, CaCl$_2$ 5 mM, and 1% BSA) for 30 min at 37° C. HUVECs were harvested with trypsin-EDTA and allowed to recover at 37° C. in complete medium for at least 1 hr. The cells were then washed free of serum and resuspended at 1×10$^6$ cells/mL in control medium followed by addition to the coated wells (200 μL) and incubation at 37° C. for 90 min. After incubation, the slides were washed gently three times with DPBS and the adherent cells were fixed and stained as above. Five high power fields per well in triplicate were counted to determine the number of cells attached to the different substrata. Data are expressed as percentage of control cell adhesion (x±SEM, n=3).

Figure 2A:
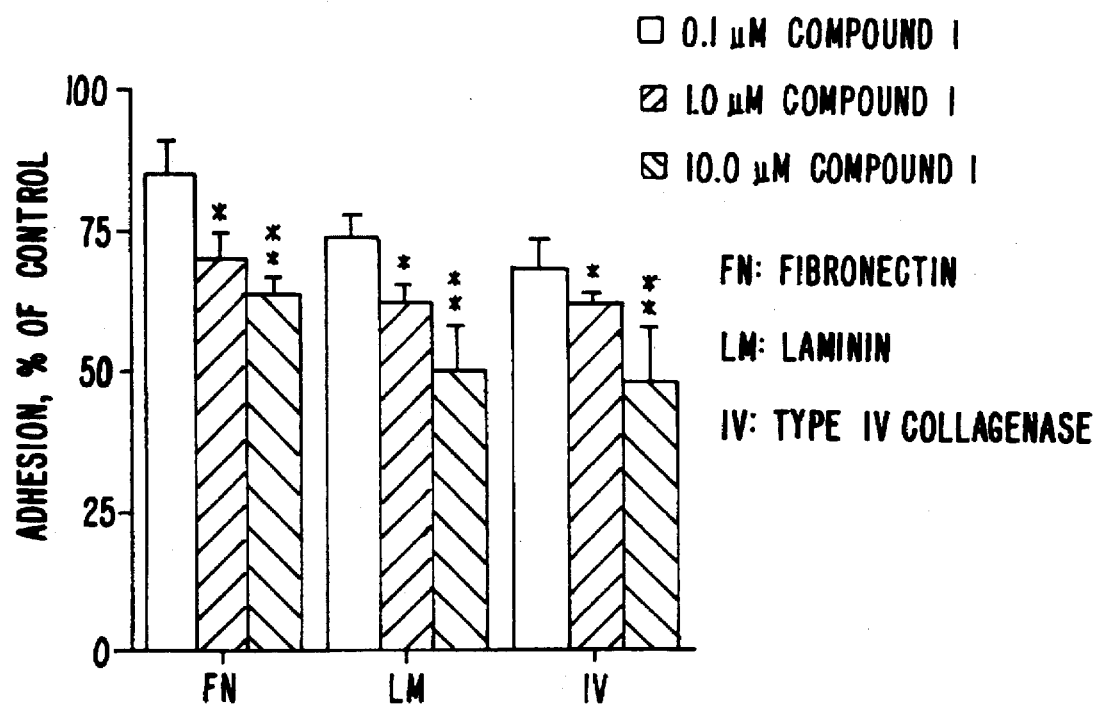
FIG. 2A shows inhibition of HUVEC adhesion by compound 1.

As shown in FIG. 2A, the adhesion of HUVECs to all substrata tested was inhibited in a dose-dependent fashion by a 18 hr pretreatment of HUVECs with compound 1 (0–10 μM). The inhibitory effect of compound 1 on HUVEC adhesion was statistically significant for laminin, fibronectin, and collagen type IV at 1.0 μM (P2<0.04, 0.043, and 0.027, respectively) and 10.0 μM (p2<0.004, 0.011, and 0.025, respectively). Preincubation of HUVECs with compound 1 did not significantly inhibit adhesion to gelatin, and therefore, gelatin was chosen as the substratum for filter coating for the motility assays.

A modified Boyden chamber system was used to determine whether compound 1 could modulate the chemotactic stimulation of endothelial cells by fibronectin, laminin, type IV collagen or thrombospondin. The particular system used has been described for tumor cell motility. See, Minniti, et al., *J. Biol. Chem.* 267:9000–9004 (1992). Modifications were made as to cell number, membrane pore size, and time of incubation were tested to determine optimal conditions for the HUVECs.

HUVECs were pretreated as described above for adhesion and resuspended at 2×10$^6$ cells/mL in M-199 containing 0.1% bovine serum albumin. Cells were seeded in the upper compartment of the chamber separated from the lower compartment by a gelatin-coated Nucleopore filter with 8μ pores. Laminin (100 μg/mL), fibronectin (30 μg/mL), type IV collagen (100 μg/mL) or thrombospondin (20 μg/mL)

were diluted from stock solutions into control medium (M-199 plus 0.1% BSA) and were used as chemoattractants in the lower chamber. HUVECs were incubated with DMSO control (0.1%) or compound 1 (0.1–10 µM) for 18 hr prior to the motility assay. Compound 1 and DMSO were maintained with the cells throughout the experiment. Assays were incubated at 37° C. for 2 hours after which the filters were removed, fixed, and stained. Cell migration was quantited by counting five high power fields in triplicate pellets of migrated cells. Results are expressed as percentage of control cell migration (x±SEM, n=3).

Figure 2B:
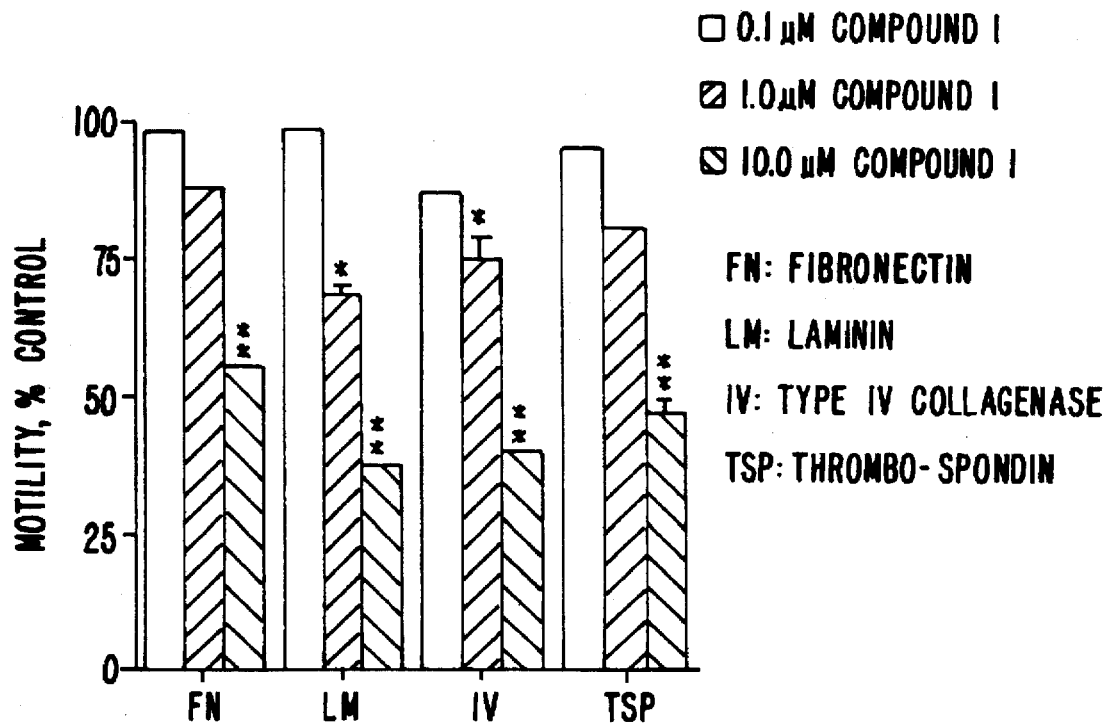
FIG. 2B shows the dose-dependent inhibition of HUVEC motility by compound 1.

As FIG. 2B shows, compound 1 caused a statistically significant dose-dependent inhibition of HUVEC motility towards laminin and type IV collagen at 1 µM (*P2<0.009, P2, 0.018) and towards all attractants at 10 µM (fibronectin, laminin, type IV collagen and thrombospondin, **p2<0.001).

These findings demonstrate selective inhibition of HUVEC adhesion and migration to extracellular matrix components, with the most significant effects seen for the major components of basement membrane, laminin and type IV collagen.

EXAMPLE 3

Inhibition of HUVEC MMP-2 gelatinolytic activity by compound 1.

This example illustrates the effect of compound 1 on gelatinolytic activity and metalloproteinase production in HUVECs.

Angiogenesis is characterized by a local degradation of subendothelial basement membrane by endothelial cell-secreted gelatinases. Aliquots of concentrated HUVEC conditioned medium from compound 1-treated and control cells were subjected to gelatin zymography, in order to test the effect of compound 1 on metalloproteinase production.

Gelatin zymography was carried out as described in Brown, et al., *Cancer Research* 50:6184–6191 (1990). HUVECs were seeded at $1.2 \times 10^5/cm^2$ in 25 $cm^2$ fibronectin-coated tissue culture flasks in complete medium containing increasing concentrations of compound 1 (0.1–10 µM) or DMSO vehicle control. After 18 hr of culture, the complete medium was removed and the cells were washed once with serum-free M-199 supplemented with 5 µg/mL bovine insulin, 5 µg/mL human transferrin and 5 ng/mL sodium selenite (ITS). A further 24 hr incubation was carried out with 3 mL of fresh ITS-containing M-199 and varying concentrations of compound 1 (0.1–10 µM) or DMSO vehicle control (0.1%). This conditioned medium was harvested and spun free of cells.

Figure 3A:
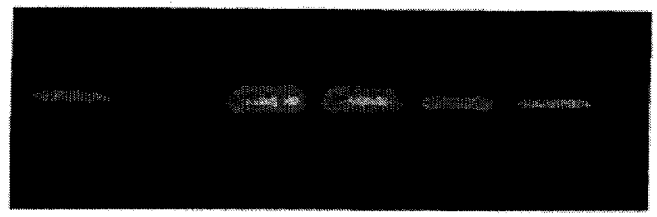
FIG. 3 shows the effect of compound 1 on gelatinase activity and proteinase expression of HUVECs.

FIG. 3A shows the dose-dependent inhibition of MMP-2 gelatinase activity (gelatinase A/72 kDa type IV collagenase). Conditioned medium (CM) from HUVECs treated with DMSO vehicle or increasing concentrations of compound 1 (0.1–10 µM) were subjected to SDS-PAGE zymography. Lane 1: CM from DMSO-treated HUVECs; lanes 2–4: CM from HUVECs treated with 0.1, 1 and 10 µM compound 1, respectively. Conditioned medium from HT1080 human fibrosarcoma cells was used as standard for the MMP-9 (gelatinase B/92 kDa type IV collagenase) and the MMP-2 gelatinases as labelled.

Treatment of HUVECs for 24 hr with increasing concentrations of compound 1 resulted in a dose-dependent inhibition of proMMP-2 latent type IV collagenase/gelatinase A and of its activated form at 62 kDa (MMP-2). Densitometric analysis showed that 10.0 µM compound 1 caused a 50% decrease in MMP-2. Similar results were obtained after 48 hr incubation with compound 1 (not shown). No gelatinolytic activity corresponding to MMP-9 (92 kD/gelatinase B) was detectable in the conditioned media of HUVECs.

Figure 3B:

The production of metalloproteinases in endothelial cells has been shown to be stimulated by bFGF. See, Rifkin, et al., *J. Cell Biol.* 109:1–6 (1989). To test the effect of compound 1 on cytokine-stimulated production of MMPs, the HUVECs were cultured as described above, however bFGF at a final concentration of 10 ng/mL was added for the final 24 hr of incubation. Precast 10% SDS-PAGE gels containing 1 mg/mL gelatin were loaded with 15 µL of 3-fold concentrated conditioned medium mixed with denaturing but non-reducing sample buffer. After electrophoresis, the gel was rinsed twice with 2.5% Triton X-100 to remove the SDS and to allow the gelatinases to renature. The gel was then incubated overnight at 37° C. in low salt collagenase substrate buffer which contained 5 mM $CaCl_2$ after which it was stained with Coomassie blue. The resulting zymogram is shown in FIG. 3B. Lane 1 corresponds to DMSO-treated HUVECs (control). Lanes 2 and 3 correspond to HUVECs treated with compound 1 (10 µM) and bFGF (10 ng/mL) respectively. Lane 4 corresponds to HUVECs treated with both bFGF and compound 1 at the levels used in lanes 2 and 3. The gelatinase activities were identified as clear bands against the blue stained gelatin gel background. Conditioned medium from HT1080 tumor cells was used as the standard for identification of the 92 kDa MMP-9/gelatinase B and the 72 kDa MMP-2/gelatinase A and confirmed by Western immunoblot using peptide-specific polyclonal antiserum (not shown, gift of William Stetler-Stevenson, Laboratory of Pathology, NCI).

As FIG. 3B indicates, compound 1 reduced bFGF-stimulated synthesis of proMMP-2 and its activated form in HUVECs (90% inhibition). Northern analysis was used to determine if this effect occurred at the level of MMP-2 expression.

HUVECs were grown to confluence as described. Fresh complete medium with test compounds was added to confluent cells for an additional 24 hr incubation. bFGF (10 ng/mL), and/or compound 1 (10 µM) or DMSO control (0.1%) were added as indicated below. Total RNA was isolated by the guanidine isothiocyanate/CsCl method. Aliquots of RNA (7.5 µg) were separated on 1% agarose/ formaldehyde gels, passively transferred to GeneScreen Plus membrane in 20X SSC, then cross-linked with ultraviolet light. Blots were prewashed for 1 hr at 42° C. in 1M NaCl, 10 mM Tris, 1 mM EDTA, 0.1% SDS and then hybridized overnight at 42° C. with a formamide-containing buffer (hybridization buffer final: 50% formamide, 4X SSC, 10 mM Tris pH 7.5, IX Denhardt solution, 0.2% SDS, 125 µg/ml salmon sperm DNA) with a random-primed 300 bp insert for MMP-2 (gift of Dr. William Stetler-Stevenson, Laboratory of Pathology, NCI). Blots were washed under stringent conditions then exposed to film. After removal of MMP-2 probe, blots were rehybridized with β-actin probe for quantitation of the RNA load. Results were quantitated by densitometric evaluation of the autoradiographs.

Figure 3C:
Figure 3C:

FIG. 3C shows the resulting Northern analysis. Lane 1 corresponds to the mRNA from HUVECs treated with DMSO (control). Lanes 2–4 show the mRNA isolated from HUVECs treated with compound 1 (10 µM) alone, compound 1 (10 µM) and bFGF (10 ng/mL), bFGF (10 ng/mL) alone, respectively. The relative abundance of each mRNA corrected for loading is shown in Table 1. Exposure to compound 1 decreased native MMP-2 expression by 86%, whereas exposure to 10 ng/mL bFGF and compound 1 for 24 hr, resulted in a net decrease of 62%.

TABLE 1

Quantitation of Northern blot analysis of MMP-2 expression

|  | MMP-2* | β-actin* | Corrected values | % Inhibition |
|---|---|---|---|---|
| Control | 139 | 66 | 2.09 | 86 |
| Control + Compound 1 | 38 | 127 | 0.30 |  |
| bFGF | 77 | 205 | 0.37 | 62 |
| bFGF + Compound 1 | 31 | 210 | 0.14 |  |

*Densitometer units

These results show that compound 1 inhibits the production of MMP-2/gelatinase A in HUVECs under native and bFGF-induced conditions and indicate that part or all of this effect may occur at the level of expression.

EXAMPLE 4

Inhibition of vascular tube formation on Matrigel.

The example illustrates the effect of compound 1 on in vitro tube formation.

HUVECs plated on a layer of Matrigel have been shown to stop proliferation and undergo a rapid morphological rearrangement. After 12–24 hours, this rearrangement leads to the development of a network of tube-like structures that resemble capillaries. See, Kubota, et al., *J. Cell Biol.* 107:1589–1598 (1988).

Figure 4A:
FIG. 4 shows the influence of compound 1 on in vitro angiogenesis of HUVECs plated on Matrigel.
Figure 4B:
Figure 5A:
FIG. 5 shows the inhibition of in vivo angiogenesis by compound 1 using the chick chorioallantoic membrane assay.
Figure 5B:
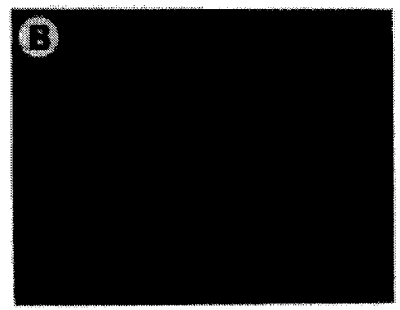
Figure 5C:
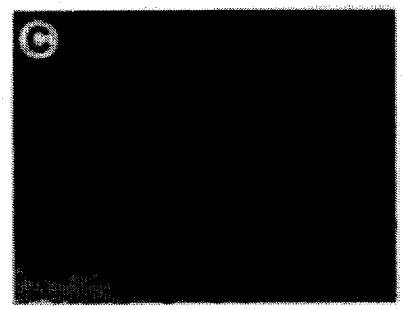
Figure 5D:

Matrigel is a solution of murine basement membrane enriched for laminin and collagen type IV and has been used previously as a permissive substrate for vessel formation. See, Albini, et al., *Int. J. Oncol.* 1:723–730 (1992). The effect of compound 1 on in vitro tube formation was tested using this system. Individual wells of 24 well plates were coated with a 300 µL aliquot of concentrated Matrigel solution (10 mg/mL) and allowed to solidify for 1 hr at 37° C. Compound 1 (1.0, 10 or 20 µM) or DMSO control (0.1%) was added to Matrigel and to the culture media. HUVECs (50,000 cells/well) were incubated on the Matrigel in complete medium for 24 hr then evaluated by phase contrast microscopy and photographed. Similar results were seen when compound 1 was present only in the media (FIGS. 4A and 4B). The multicellular tubes were less extensive, thinner, foreshortened, and less cellular when compared with DMSO control cultures. Treatment with 20 µM compound 1 resulted in a more striking inhibition of tube formation; similar results were obtained when compound 1 was omitted from the Matrigel (data not shown).

These findings show that the individual inhibitory effects of compound 1 against adhesion, migration, and proteolysis may be manifest together as inhibition of coordinated endothelial function of vessel formation in an in vitro model.

EXAMPLE 5

Inhibition of angiogenesis in vivo.

This example illustrates the ability of compound 1 to inhibit angiogenesis in vivo using the chick chorioallantoic membrane assay.

The chick chorioallantoic or yolk sac membrane (CAM) assays for angiogenesis are important in vivo models of microvessel formation. The assay was conducted using the method of Taylor and Folkman, *Nature* 297:307–311 (1982). Briefly, fertilized chick embryos with the yolk intact were removed from their shells on day 3 of development and incubated at 37° C. The following day a 0.5% methylcellulose disk containing compound 1 (10 or 20 µM), AIC (10 µM) or DMSO (0.05%) was placed at the advacing edge of the vascular membrane. After 48 hr of exposure to compound 1, the membranes were evaluated and photographed. FIG. 5 shows the results of this assay for DMSO vehicle control (panel A, 50 X); compound 1 20 µM (panel B, 50 X); AIC inactive compound 1 analogue (panel C, 12X); and compound 1 20 µM (panel D, 12X). Inhibition of angiogenesis was demonstrated by an avascular zone surrounding the compound 1-containing disk. AIC, an inactive compound 1 analogue, was tested as a negative control. Methylcellulose disks with DMSO (0.05%) or hydrocortisone (60 µg) were tested under similar conditions as negative and positive controls, respectively.

The angiogenesis inhibitory effect of compound 1 was dose-dependent. A large avascular zone was present in 55% of embryos treated with 10 µM compound 1 and in 67% of embryos treated with 20 µM compound 1 (Table 2).

TABLE 2

Compound 1 inhibits capillary formation in vivo

| Agent | Eggs with avascular zones/total | % Inhibition |
|---|---|---|
| Compound 1 (10 µM) | 19/34 | 55 |
| Compound 1 (20 µM) | 20/30 | 67 |
| AIC (10 µM)* | 4/24 | 16 |
| DMSO (0.05%) | 5/42 | 9 |
| Hydrocortisone (60µ) | 10/18 | 55 |

*AIC: aminoimidazole carboxamide, inactive compound 1 analog.

These findings indicate that the in vitro results of compound 1 inhibition of proliferation, adhesion, motility, proteolysis, and tube formation are good surrogate markers for true in vivo inhibition of angiogenesis by compound 1 and show the similar dose dependence of compound 1 effects.

EXAMPLE 6

Compound 1 inhibits tyrosine phosphorylation in response to bFGF.

This example illustrates the effect of compound 1 on bFGF-induced tyrosine phosphorylation.

Basic FGF is one of the most potent angiogenic factors defined to date. It exerts its activity through activation of the bFGF receptor kinase with subsequent autophosphorylation of its receptor as well as phosphorylation of other signaling proteins. See, Jaye, et al., *Biochim. Biophys. Acta* 1135:185–199 (1992). Phosphotyrosine immunoprecipitation and Western analysis were used to investigate the effect of compound 1 on bFGF-mediated tyrosine phosphorylation.

HUVECs were grown to confluence on 10 cm culture dishes, starved with 1% FCS for 24 hr, and preincubated with compound 1 (at indicated concentrations) for 24 hr. The following day, cells were exposed to bFGF, 10 ng/mL for 15 min at 37° C. Cells were quickly washed with cold DPBS, scraped from the plate and lysed with lysis buffer (50 mM Tris-HCl pH 7.6, 300 mM NaCl, 10 µg/mL aprotinin, 1 mM phenylmethylsulphonylfluoride (PMSF), 400 µM sodium orthovanadate, 400 µM EDTA, 100 mM sodium fluoride, 100 mM sodium pyrophosphate, and 0.5% Triton-X 100) for 1 hr on ice. The lysates were centrifuged at 4° C. at 1200×g for 15 minutes after which the supernatants were saved and protein concentration determined using bicinchoninic assay protein detection method. Aliquots of lysis protein (300 mg per sample) were incubated with 10 µg of anti-phosphotyrosine monoclonal antibody, 4G10, preconjugated to protein A-sepharose beads for 1 hr at 4° C. The beads were washed three times with buffer containing 0.1% Triton X-100 and then the immunoprecipitated proteins were eluted with 2X Laemmli sample buffer and subjected to 4–12% gradient gel electrophoresis. Proteins were transferred electrically, blocked (7.5% glycine, 5% dry milk, 1% ovalbumin) for 30 min at room temperature, then washed (0.001% ovalbumin, 0.001% dry milk, 0.001% Tween-20 in phosphate-buffered saline (PBS)). Immunoblots were incubated overnight with 4G10 anti-phosphotyrosine monoclonal antibody (1 µg/mL). After three washes, the immunocomplexes were visualized after reaction with 0.5 µCi/mL of $^{125}$I-labeled protein A for 1 hr at room temperature. Blots were exposed to film for 24–72 hours.

Figure 6:
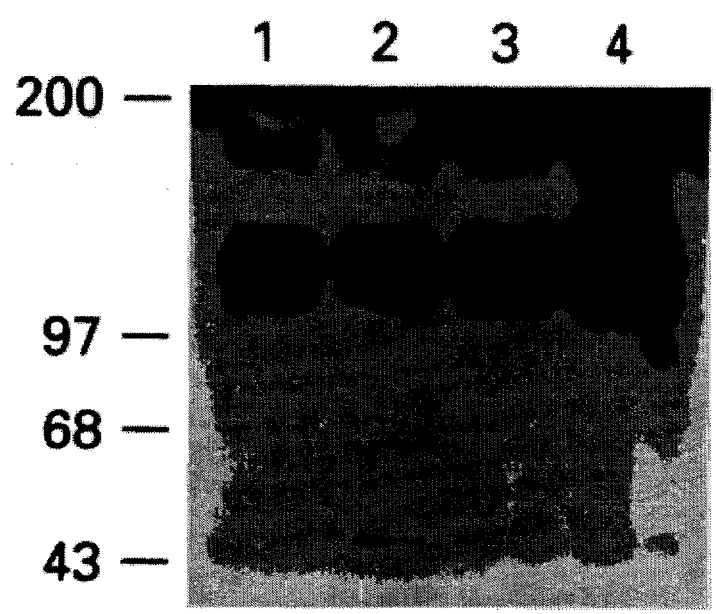
FIG. 6 shows the inhibition of phosphotyrosine phosphorylation events in bFGF-stimulated HUVECs by compound 1.

FIG. 6 shows the bFGF-induced stimulation of tyrosine phosphorylation. The size of the main band is approximately 110–150 kDa, representing the range of molecular weight for bFGF receptors. Neither DMSO control (lane 1) or compound 1 (10 µM, lane 2) altered basal tyrosine phosphorylation, however, incubation of HUVECs with compound 1 (10 µM) for 18 hr with concomitant exposure to bFGF (10 ng/mL) for the final 15 minutes resulted in inhibition of bFGF-stimulated phosphorylation as shown in lane 3. Thus, treatment of HUVECs with compound 1 blocked bFGF-stimulated tyrosine phosphorylation, including autophosphorylation of bFGF receptor (bFGF, lane 4).

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A method of treating diseases associated with angiogenesis in a host, comprising treating said host with an effective amount of a compound of formula:

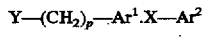

wherein:

p is an integer of from 0 to 4;

$Ar^1$ and $Ar^2$ are each aromatic moieties independently selected from the group consisting of phenyl, naphthyl, and substituted versions thereof in which the substituents are members selected from the group consisting of halogen, nitro, carboxyl and alkoxy;

X is a linking moiety selected from the group consisting of O, S, $SO_2$, CO, CHCN, straight chain alkyl, alkoxy, and alkoxyalkyl; and Y is a nitrogen-containing heterocyclic moiety of the formula

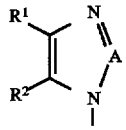

(II)

wherein:

A is N or CH, $R^1$ is a member selected from the group consisting of hydrogen, —$CONH_2$, —$CONHR^5$, —$CO_2H$, —$CO_2R^5$, —$SO_2NH_2$, $R^2$ is a member selected from the group consisting of hydrogen, —$NH_2$, —$NHCOC_6H_5$, —$NHCOR^5$, —NHCHO, —$NHR^5$, —$N(R^5)_2$ and $R^5$ is lower alkyl of from 1 to 6 carbon atoms; said diseases being members selected from the group consisting of diabetic retinopathy, hemangiomata, collagen vasculidities, and proliferative nephropathies.

2. A method in accordance with claim 1 wherein Y is a radical of formula (II) and A is N.

3. A method in accordance with claim 1 wherein Y is a radical of formula (II), A is N, and $R^1$ is a member selected from the group consisting of hydrogen, —$CONH_2$, —$CONHR^5$, and —$CO_2H$.

4. A method in accordance with claim 1 wherein Y is a radical of formula (II), A is N, and $R^1$ is —$CONH_2$.

5. A method in accordance with claim 1 wherein Y is a radical of formula (II), A is N, $R^1$ is —$CONH_2$, and $R^2$ is —$NH_2$.

6. A method in accordance with claim 1 wherein p is an integer of from 0 to 2, $Ar^1$ and $Ar^2$ are both substituted phenyl, X is a linking moiety selected from the group consisting of O, CO, and CHCN, Y is a radical of formula (II), $R^1$ is —$CONH_2$, and $R^2$ is —$NH_2$.

7. A method in accordance with claim 1 wherein p is 1, $Ar^1$ is 2,6-dichlorophenyl, $Ar^2$ is 4-chlorophenyl, X is CO, Y is a radical of formula (II), A is N, $R^1$ is —$CONH_2$, and $R^2$ is —$NH_2$.

* * * * *